United States Patent [19]

Atkins et al.

[11] Patent Number: 5,110,992
[45] Date of Patent: May 5, 1992

[54] PROCESS FOR THE PREPARATION OF GLYCOL ETHERS

[75] Inventors: Martin P. Atkins, Sunbury-on-Thames; William Jones, Cambridge; Malama Chibwe, Romford, all of England

[73] Assignee: The British Petroleum Co., p.l.c., London, England

[21] Appl. No.: 586,826

[22] Filed: Sep. 24, 1990

[30] Foreign Application Priority Data

Oct. 4, 1989 [GB] United Kingdom ............. 8922358.0

[51] Int. Cl.⁵ .................. C07C 43/03; C07C 43/10
[52] U.S. Cl. .................... 568/618; 568/678; 568/670; 568/648; 568/608
[58] Field of Search ................ 568/678, 618

[56] References Cited

U.S. PATENT DOCUMENTS

| | | | |
|---|---|---|---|
| 3,879,523 | 4/1975 | Miyata | 423/250 |
| 3,879,525 | 4/1975 | Miyata | 423/277 |
| 4,458,026 | 7/1984 | Reichle | 502/80 |
| 4,476,324 | 10/1984 | Reichle | 568/388 |
| 4,774,212 | 9/1988 | Drezdon | 502/62 |
| 4,962,237 | 10/1990 | Laycock | 568/618 |

FOREIGN PATENT DOCUMENTS 5603643 9/1979 Japan.
2179563 3/1987 United Kingdom.

OTHER PUBLICATIONS

"Anionic Clay Minerals", W. T. Reichle, Chemtech, Jan. 1986.
Reichle et al., J. Catal., 101, 352-359 (1986).

*Primary Examiner*—Howard T. Mars
*Assistant Examiner*—Rebecca Cook
*Attorney, Agent, or Firm*—Larry W. Evans; Joseph G. Curatolo; Sue E. Phillips

[57] ABSTRACT

A process for the preparation of a glycol ether by reacting an olefin oxide with an excess of an alcohol over a catalyst; characterized in that the catalyst comprises a material which has been prepared by calcination of an anionic double hydroxide clay having a structure comprising magnesium and aluminum in combination, followed by rehydration and subsequent recalcination.

9 Claims, 2 Drawing Sheets

PROCESS FOR THE PREPARATION OF GLYCOL ETHERS

This invention relates to a process for the preparation of glycol ethers.

Glycol ethers are useful as jet anti-icing fluids, brake fluid blending components and solvents for paints, inks and the like. They may be produced by reacting an alcohol with an olefin oxide in the presence of either a basic or acidic catalyst.

Anionic double hydroxide clays are well-known materials. They are described in, for example, "Anionic Clay Minerals", W. T. Reichle, "Chemtec", January 1986. They consists of positively charged metal oxide/hydroxide sheets with intercalated anions and water molecules. In terms of charge they are mirror-images of the much studied family of cationic clay minerals. The structure of anionic double hydroxide clays is related to that of brucite, $Mg(OH)_2$. In brucite magnesium is octahedrally surrounded by six oxygens in the form of hydroxide; the octahedral units then, through edge sharing, form infinite sheets. The sheets are stacked on top of each other by hydrogen bonds. If some of the magnesium in the lattice is isomorphously replaced by a higher charged cation, e.g. $Al^{3+}$, then the resulting overall single $Mg^{2+}$—$Al^{3+}$—OH layer gains a positive charge. Sorption of an equivalent amount of hydrated anions renders the structure electrically neutral, resulting in an anionic double hydroxide clay.

Anionic double hydroxide clays have, in the dehydrated form, the empirical formula:

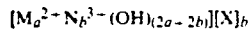

in which $M^{2+}$ is a divalent metal cation; $N^{3+}$ is a trivalent metal cation; X is one equivalent of an anion; and a and b represent the relative proportions of M and N in the structure. Typically, $M^{2+}$ is $Mg^{2+}$, $Fe^{2+}$, $Co^{2+}$, $Ni^{2+}$ and/or $Zn^{2+}$, and $N^{3+}$ is $Al^{3+}$, $Cr^{3+}$ and/or $Fe^{3+}$. In an alternative form, the divalent metal may be wholly or partly replaced by lithium, the all-lithium form having the empirical formula:

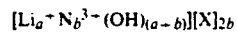

In the naturally-occurring minerals hydrotalcite and mannaseite, $M^{2+}$ is $Mg^{2+}$, $N^{3+}$ is $Al^{3+}$, X is carbonate, and a/b is in the range of 1:1 to 5:1. Such minerals occur in a hydrated form.

U.S. Pat. No. 4,458,026 discloses that catalysts prepared by calcination of anionic double hydroxide clays may be used to perform aldol condensations.

Figure 1:
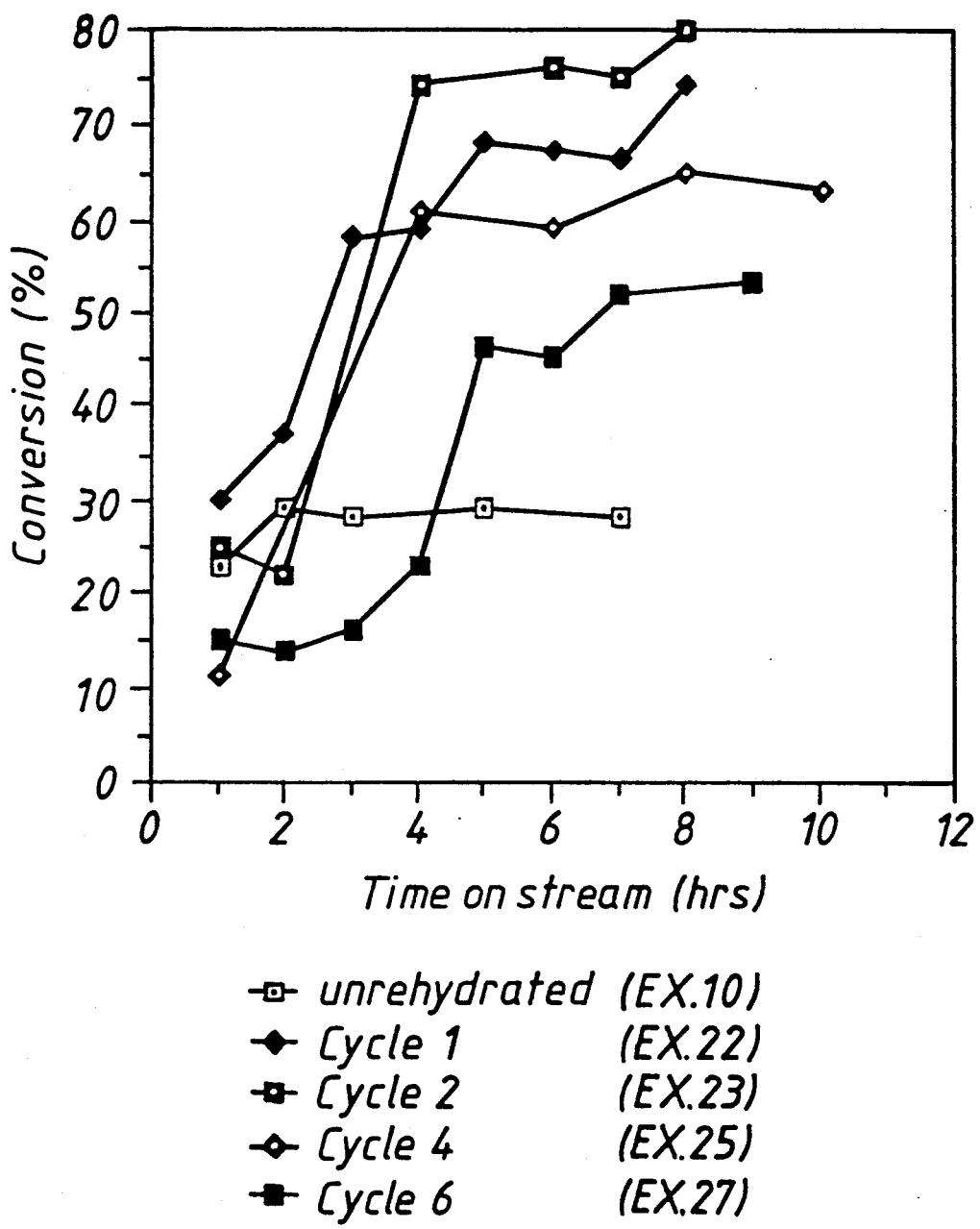
FIG. 1 is a graph showing the percent of conversion of propylene oxide versus the time on stream for glycol ether preparation using the method of the present invention and using a method which does not use a rehydrated and calcined catalyst.

The present invention provides a process for the preparation of a glycol ether by reacting an olefin oxide with an excess of an alcohol over a catalyst; characterised in that the catalyst comprises a material which has been prepared by calcination of an anionic double hydroxide clay.

Preferably the anionic double hydroxide clay has a framework structure comprising magnesium and aluminium.

Anionic double hydroxide clays can be prepared by known methods, for example by the method described in U.S. Pat. No. 4,458,026. In general, solutions of soluble salts of the relevant metals are mixed together with an alkali metal hydroxide and an alkali metal carbonate. The resulting mixture is vigorously stirred until a slurry is formed. The slurry is then heated, typically to a temperature between 50° and 100° C., preferably 60° to 75° C., until sufficient crystallisation occurs.

In order to prepare the catalyst required for the process of the invention, the anionic double hydroxide clay is subjected to calcination. Preferably this involves heating to a temperature of at least 300° C., preferably 300° to 550° C., especially 400° to 500° C., under non-reducing conditions. The heating may be carried out under vacuum, in an inert gas or, preferably, in an oxidising atmosphere, preferably air. Heating is carried out for a period of time typically between 10 and 30 hours. Such treatment causes the collapse of the double hydroxide layered structure, and, generally, results in an oxide material having a structure related to that of MgO.

The calcined anionic double hydroxide clay may be used directly as the catalyst for the preparation of glycol ethers. However, we have found that the catalytic activity of the material is enhanced if the calcined material is rehydrated and subsequently recalcined. Such procedure is particularly effective when the rehydration is carried out using water substantially free from dissolved ions, particularly decarbonated water. Suitable decarbonated water may be prepared by purging distilled or deionised water with an inert gas, for example nitrogen, argon or hydrogen, to remove carbon dioxide and hence carbonate ions. Rehydration may be carried out simply by soaking for an adequate period of time, typically from 10 to 30 hours, and then recalcining the material by the same method as used for the initial calcination. Such rehydration/recalcination treatment may if desired be carried out a number of times, with beneficial results, especially when using a material containing magnesium and aluminium.

The alcohol used in the process according to the invention may be an aliphatic, cycloaliphatic or aromatic alcohol, preferably having up to 8 carbon atoms. An aliphatic alcohol preferably has up to 6, more preferably up to 4, carbon atoms. Typical aliphatic alcohols include methanol and ethanol. An example of a suitable cycloaliphatic alcohol is cyclohexanol, and an example of a suitable aromatic alcohol is phenol. More than one alcohol group may be present if desired, but preferably the alcohol is a mono alcohol. Mixtures of alcohols may be used if desired. The alcohol must be used in excess to produce the desired glycol ether and suppress the formation of oligomeric products. Preferably the molar ratio of alcohol to olefin oxide is at least 2:1, especially at least 5:1, most preferably at least 10:1.

The olefin oxide preferably has up to 10, especially up to 8, carbon atoms, and may for example be derived from an alkene, for example ethene or propene, or from an arylalkene such as styrene.

In a preferred embodiment of the invention, ethanol is reacted with propylene oxide to produce a mixture of the primary and secondary glycol ethers, 2-ethoxy-1-propanol and 1-ethoxy-2-propanol. It is a major advantage of the process according to the present invention that the reaction proceeds with a very high selectivity to the secondary product, which is in general the desired product.

The reaction may be carried out in the vapour phase or, especially, the liquid phase. The optimum reaction temperature will of course depend upon the particular reactants used, but will in general be within the range of from 0° to 200° C., especially 70° to 150° C. The reaction may be carried out at atmospheric or elevated pressure, for example up to 100 barg.

The following Examples illustrate the invention. Examples 1 to 8 illustrate the synthesis of anionic double hydroxide clays; Examples 9 and 22 to 28 illustrate calcination of anionic double hydroxide clays to produce active catalysts; and Examples 10 to 21 and 29 to 33 illustrate the use of these catalysts in the production of glycol ethers. Example 34 is a comparative example.

EXAMPLE 1

Preparation of a Magnesium/Aluminium/Carbonate Anionic Double Hydroxide Clay

A solution of 256 g $Mg(NO_3)_2.6H_2O$ (1.00 mole) and 187.5 g $Al(NO_3)_3.9H_2O$ (0.50 moles) in 700 ml deionised water was added dropwise to a solution of 140 g NaOH (3.5 mole) and 100 g anhydrous $Na_2CO_3$ (0.943 mole) in 1000 ml deionised water. The addition was carried out in a 3 liter flask and uniform mixing was achieved by use of a mechanical stirrer. Using a cooling bath, the temperature was maintained at about 35° C. during solution which took about 4 hours. A heavy slurry was formed. The flask contents were then transferred to a thermal bath and heated to and maintained at 65±2° C. for 18 hours with continuous stirring. Thereafter the resulting thick slurry was filtered and washed with a large excess of deionised water. The solid was then dried at 125° C. either in vacuum or air for 18 hours. The resulting white powder gave an X-ray powder diffraction profile of hydrotalcite. This profile is shown in Table XRD-1.

Elemental analysis: 11.99% Al; 19.08% Mg; 2.60% C. This corresponds to an empirical formula of $Mg_6Al_{3.3}(OH)_{18.6}(CO_3)_{1.7}4H_2O$.

$^{27}Al$ magic angle spinning nmr gave a single peak of chemical shift 8.3 ppm, corresponding to all the aluminium being in octahedral coordination.

EXAMPLE 2

Preparation of a Magnesium/Iron/Carbonate Anionic Double Hydroxide Clay

Example 1 was repeated except that a solution of 25.6 g $Mg(NO_3)_2.6H_2O$ (0.10 moles) and 13.45 g $Fe(NO_3)_3.9H_2O$ (0.033 moles) in 70 ml water was added dropwise to a 100 ml solution of NaOH (12 g, 0.30 mole) and $Na_2CO_3$ (10 g, 0.094 moles). The XRD of the product is shown in Table XRD-2.

Elemental analysis: 2.09% C; 21.3% Mg; 17.9% Fe. This corresponds to an empirical formula of $Mg_6Fe_{2.2}(OH)_{16.4}(CO_3)_{1.1}4H_2O$.

EXAMPLE 3

Preparation of a Nickel/Aluminium/Carbonate Anionic Double Hydroxide Clay

Example 1 was repeated except that a solution of $Ni(NO_3)_3.6H_2O$ (29.1 g, 0.10 moles) and $Al(NO_3)_3.9H_2O$ (12.5 g, 0.033 moles) in 70 ml deionised water was added slowly to an aqueous solution of NaOH (12.0 g, 0.30 moles) and $Na_2CO_3$ (10 g, 0.094 moles) in 100 ml deionised water. The XRD of the product is shown in Table XRD-3.

Elemental analysis: 1.75% C.

EXAMPLE 4

Preparation of a Zinc/Chromium/Carbonate Anionic Double Hydroxide Clay

Example 1 was repeated except that a solution of $Zn(NO_3)_2.6H_2O$ (29.8 g, 0.10 moles) and $Cr(NO_3)_3.9H_2O$ (13.3 g, 0.033 moles) in 70 ml deionised water was added to a solution of $Na_2CO_3$ (31.8 g, 0.30 moles) in 300 ml deionised water at room temperature. The XRD of the product is shown in Table XRD-4.

Elemental analysis: 2.85% C; 44.7% Zn; 10.7% Cr. This corresponds to an empirical formula of $Zn_6Cr_{1.8}(OH)_{15.6}(CO_3)_{0.9}4H_2O$.

EXAMPLE 5

Preparation of a Lithium/Aluminium/Carbonate Anionic Double Hydroxide Clay

A total amount of 250 ml of a 0.4M $AlCl_3.6H_2O$ solution was added dropwise to 600 ml of a mixture of 1.5M $LiOH.H_2O$ and 0.08M $Na_2CO_3$ with vigorous stirring. The addition took 40-45 minutes. The gel-type precipitate was then heated at 65° C.±2 in a thermal bath with gentle stirring for about 18 hours. On cooling the white slurry was filtered and washed using hot deionised water. This was later dried at 70° C. in air overnight. The X-ray powder diffraction profile, Table XRD-5, was that of an anionic double hydroxide clay.

Elemental analysis: 2.95% C; 3.05% Li; 22.4% Al.

EXAMPLE 6

Preparation of Magnesium/Chromium/Carbonate Anionic Double Hydroxide Clay

A solution of $[Cr(H_2O)_6]Cl_3$ (178 g, 0.67 moles) and $[Mg(H_2O)_6]Cl_2$ (407 g, 2.00 moles) in 1.4 dm$^3$ of distilled water was added at a rate of about 12 cm$^3$/minute to a vigorously stirred solution of $Na_2CO_3$ (200 g, 1.89 moles) and NaOH (280 g, 7.00 moles) in 2 dm$^3$ of distilled water. The resulting reaction mixture was then heated to 65° C. for 18 hours. Vigorous stirring was maintained throughout this period. The slurry was then allowed to cool to room temperature. During this time the precipitate partially settles from its mother liquor. The supernatant was decanted and the slurry was concentrated by centrifuging (2000 rpm, about 1120 G, 1 hour) and decanting. The concentrated slurry was then loaded into dialysis tubing (Medicell Visking size 6-27/32"). The sealed tubes were then continuously washed in distilled water until the effluent water was chloride free (tested by 0.1 mol dm$^{-3}$ $AgNO_3$ solution) and the conductivity was below 20 $\mu S$ cm$^{-1}$. The dialysis tubes were then opened and the recovered slurry was slowly dried in a fan oven at 60° C.

EXAMPLE 7

Preparation of Zinc/Aluminium/Carbonate Anionic Double Hydroxide Clay

This material was made using a similar procedure described for the Mg-Cr system above. A solution of $[Al(H_2O)_6]Cl_3$ (162 g, 0.67 moles) and $[Zn(H_2O)_6]Cl_2$ (489 g, 2.00 moles) in 1.4 dm$^3$ of distilled water was added to a solution of $Na_2CO_3$ (200 g, 1.89 moles) and NaOH (280 g, 7.00 moles) in 2 dm³ of distilled water. The same work-up procedure was used as described for the Mg-Cr material.

EXAMPLE 8

Preparation of Zinc/Iron (III)/Carbonate Anionic Double Hydroxide Clay

This material was made using a similar procedure described for the Mg-Cr system above. A solution of [Fe(H₂O)₆]Cl₃ (181 g, 0.67 moles) and [Zn(H₂O)₆]Cl₂ (489 g, 2.00 moles) in 1.4 dm³ of distilled water was added to a solution of Na₂CO₃ (200 g, 1.89 moles) and NaOH (280 g, 7.00 moles) in 2 dm³ of distilled water. The same work-up procedure was used as described for the Mg-Cr material.

EXAMPLE 9

Calcination

The products of Examples 1 to 8 were calcined, at 450° C. (Examples 1 to 5) or 400° C. (Examples 6 to 8 for 18 hours in air. The properties of the resulting catalysts were as follows:

| Catalyst Ref: | Starting Material Prepared As In: | Surface area (m²/g) | Elemental analysis |
|---|---|---|---|
| A (Mg/Al) | Example 1 | 180 | 16.87% Al; 27.3% Mg |
| B (Mg/Fe) | Example 2 | 150 | |
| C (Ni/Al) | Example 3 | 156 | |
| D (Zn/Cr) | Example 4 | | |
| E (Li/Al) | Example 5 | 129 | 4.55% Li; 35.5% Al |
| F (Mg/Cr) | Example 6 | | |
| G (Zn/Al) | Example 7 | | |
| H (Zn/Fe) | Example 8 | | |

X-ray diffraction patterns of the calcined materials are given in Tables XRD-6 to XRD-10.

EXAMPLES 10 TO 18

Preparation of glycol ethers

Tests were carried out in a fixed bed continuous flow reactor. A 10 dm³ feed pot contained the reactants which were pumped through the 316 stainless steel reactor (½"OD) under applied nitrogen pressure and containing pelleted catalyst. Two 1/16" thermocouples went on sides of the reactor right through to the centre of the catalyst bed. The product was collected in an ice-cooled vial and analysed immediately on a Perkin Elmer gas chromatograph equipped with a temperature programming facility. The injection port was held at 150° C. with the hot wire detector at 150° C. Helium carrier gas flowed at 25 ml/min. The column used was 5 meters × ⅛ inch O.D. stainless steel column packed with 10% carbowax 20M on 60-80 mesh chromosorb was temperature programmed at 60° C. for 6 minutes and then 12° C./min to 180° C.

EXAMPLE 10

Starting reactant mole ratio ethanol/propylene oxide 10/1. Catalyst: A; weight-6.5 g, volume-10 ml, temperature 122°±1° C., feed rate-21 ml/hr, pressure-15 bar. The results are given in Table A(1). 2° refers to the secondary glycol ether, 1-ethoxy-2-propanol, and 1° refers to the primary glycol ether, 2-ethoxy-1-propanol. Only traces (less than 70 ppm) of products other than 2° and 1° were obtained in this Example and also in Examples 8 to 15. Secondary product selectivity is defined as 2°/(2° + 1°)(%).

TABLE A(1)

| | Results of Example 10 | |
|---|---|---|
| Time on stream (hours) | % conversion of propylene oxide | 2° Product selectivity |
| 1 | 23 | 94 |
| 2 | 29 | 94 |
| 3 | 28 | 94 |
| 5 | 28 | 93 |
| 7 | 28 | 92 |

EXAMPLE 11

Starting reactant mole ratio ethanol/styrene oxide 10/1. Catalyst: A; weight-3.44 g, temperature-175°±3° C., volume-10 ml, flow rate-15 ml/hr, pressure-15 bar. The results are given in Table A(2).

TABLE A(2)

| | Results of Example 11 | |
|---|---|---|
| Time on stream (hours) | % conversion of styrene oxide | 2° Product selectivity |
| 1 | 24 | 47 |
| 3 | 37 | 36 |
| 4 | 86 | 38 |
| 5 | 91 | 46 |
| 6 | 92 | 56 |
| 7 | 92 | 56 |
| 8 | 94 | 58 |
| 9 | 93 | 54 |
| 10 | 92 | 58 |

EXAMPLE 12

Starting reactant mole ratio ethanol/propylene oxide 10/1. Catalyst: B; weight-9.17 g, volume-15 ml, temperature-121°±2° C., feed rate-30 ml/hr, pressure-15 bar. The results are given in Table B(1).

TABLE B(1)

| | Results of Example 12 | |
|---|---|---|
| Time on stream (hours) | % conversion of propylene oxide | 2° Product selectivity |
| 1 | 72 | 92 |
| 2 | 75 | 83 |
| 4 | 66 | 81 |
| 7 | 50 | 86 |
| 10 | 50 | 78 |

EXAMPLE 13

Starting reactant mole ratio ethanol/styrene oxide 10/1; Catalyst: B; weight-6.34 g, temperature-175°±2° C., volume-15 ml, flow rate-15 ml/hr, pressure-15 bar. The results are given in Table B(2).

TABLE B(2)

| | Results of Example 13 | |
|---|---|---|
| Time on stream (hours) | % conversion of styrene oxide | 2° Product selectivity |
| 1 | 6 | 49 |
| 2 | 28 | 79 |
| 3 | 71 | 57 |
| 4 | 69 | 43 |
| 5 | 69 | 51 |

TABLE B(2)-continued

| | Results of Example 13 | |
|---|---|---|
| Time on stream (hours) | % conversion of styrene oxide | 2' Product selectivity |
| 6 | 70 | 38 |
| 7 | 68 | 52 |
| 8 | 66 | 47 |
| 10 | 59 | 28 |

EXAMPLE 14

Starting reactant mole ratio ethanol/propylene oxide 10/1. Catalyst: C; weight-18.31 g, volume-30 ml, temperature-120°±0.5° C., feed rate-30 ml/hr, pressure 15 bar. The results are given in Table C.

TABLE C

| | Results of Example 14 | |
|---|---|---|
| Time on stream (hours) | % conversion of propylene oxide | 2' Product selectivity |
| 1 | 15 | 97 |
| 3 | 17 | 93 |
| 5 | 17 | 100 |
| 7 | 16 | 90 |
| 9 | 16 | 97 |

EXAMPLE 15

Starting reactant mole ratio ethanol/propylene oxide 10/1. Catalyst: D; weight-17.55 g, volume-19 ml, temperature-120°±0.5° C., feed rate-20 ml/hr, pressure-15 bar. The results are given in Table D(1).

TABLE D(1)

| | Results of Example 15 | |
|---|---|---|
| Time on stream (hours) | % conversion of propylene oxide | 2' Product selectivity |
| 1 | 26 | 100 |
| 3 | 30 | 98 |
| 5 | 34 | 100 |
| 7 | 34 | 98 |
| 9 | 33 | 97 |
| 14 | 34 | 94 |

EXAMPLE 16

Starting reactant mole ratio ethanol/propylene oxide 10/1. Catalyst D; weight-9.6 g, volume-10 ml/hr, temperature-140° C., pressure-15 bar. The results are given in Table D(2).

TABLE D(2)

| | Results of Example 16 | |
|---|---|---|
| Time on stream (hours) | % conversion of propylene oxide | 2' Product selectivity |
| 1 | 13 | 95 |
| 2 | 19 | 94 |
| 4 | 71 | 96 |
| 7 | 77 | 98 |
| 73 | 72 | 94 |

EXAMPLE 17

Starting reactant mole ratio ethanol/styrene oxide 10/1. Catalyst: D; weight-12.66 g, temperature-175°±2° C., volume-12 ml, flow rate-18.5 ml/hr, pressure-15 bar. The results are given in Table D(3).

TABLE D(3)

| | Results of Example 17 | |
|---|---|---|
| Time on stream (hours) | % conversion of styrene oxide | 2' Product selectivity |
| 2 | 27 | 50 |
| 3 | 74 | 53 |
| 4 | 93 | 69 |
| 5 | 93 | 78 |
| 6 | 92 | 80 |
| 7 | 93 | 83 |
| 8 | 90 | 80 |

EXAMPLE 18

Starting reactant molar ratio ethanol/propylene oxide 10/1. Catalyst: E; weight-8.21 g, volume-25 ml, temperature-130°±3° C., feed rate-27 ml/hr, pressure 15 bar. The results are given in Table E.

TABLE E

| | Results of Example 18 | |
|---|---|---|
| Time on stream (hours) | % conversion of propylene oxide | 2' Product selectivity |
| 2 | 38 | 95 |
| 3 | 43 | 97 |
| 5 | 34 | 100 |
| 8 | 25 | 95 |
| 9 | 25 | 96 |
| 11 | 24 | 95 |

EXAMPLES 19 TO 21

Preparation of Glycol Ethers

Tests were carried out on catalysts F, G, and H as follows. Prior to use, the materials were ground and sieved with the particle size range 0.1-1.0 mm being collected.

A premixed feed containing ethanol/propylene oxide (10:1 molar) was held in a reservoir under a blanket of dry nitrogen. The catalyst bed comprised of 10 cm$^3$ of 0.5-1.0 mm particles loaded into a three-zoned fixed-bed reactor (0.9 cm ID) with a thermowell (0.48 cm OD). Three thermocouples were used to monitor the bed temperature profile. The run start-up procedure involved pressurising the reactor to 50 barg with the liquid feed, establishing the required flow rate (20 cm$^3$ h$^{-1}$, LHSV (liquid hourly space velocity) 2) and the increasing the reactor temperature to the operating condition of 100° C. The reactor liquid effluent was collected, over set intervals, at 0° C. and atmospheric pressure. A representative reactor product effluent was obtained after 5 hours. Mass balances were typically 98% +.

The collected liquid product was analysed by gas chromatography. Two columns were used in this analysis. A Poropak QS column (1 m, 80-100 mesh, 2 mm ID, 200° C.) to obtain accurate conversion data and a CP-Sil-5 WCOT fused silica capillary column (50 m, 0.25 mm ID, 10 minute at 80° C., 8° C./minute to 200° C.) to obtain accurate selectivity data.

The results, obtained after 24 hours are given in Table F.

TABLE F

| | Results of Examples 19 to 21 | | | |
|---|---|---|---|---|
| Example No. | Catalyst | Weight of Catalyst | % Conversion of propylene oxide | 2' Product Selectivity |
| 19 | F | 9.4 | 42 | 94 |
| 20 | G | 7.6 | 6 | 84 |

TABLE F-continued

Results of Examples 19 to 21

| Example No. | Catalyst | Weight of Catalyst | % Conversion of propylene oxide | 2° Product Selectivity |
|---|---|---|---|---|
| 21 | H | 13.0 | 13 | 83 |

EXAMPLE 22

First Cycle Rehydration 10.0 g of the calcined material A prepared as in Example 9 was taken and added to 100 ml previously boiled water and cooled with bubbling $N_2$ for about an hour. The material was then left overnight. It was then washed with hot distilled water and partially dried under $N_2$ before being dried at 125° C. This material gave the XRD pattern of a regenerated anionic double hydroxide (hereafter referred to as regenerated 1st cycle) and the reflections are shown in Table XRD-11. The material was then calcined at 450° C. for 18 hours to generate the catalyst. The XRD pattern, given in Table XRD-12, showed two phases: a relatively small amount of spinel and the expected pattern of a collapsed anionic double hydroxide clay, i.e. MgO structure.

EXAMPLE 23

Second Cycle Rehydration

Example 22 was repeated using as starting material the product of Example 22. The XRD powder pattern of the rehydrated material is shown in Table XRD-13, and that of the rehydrated recalcined material in Table XRD-14.

EXAMPLE 24

Example 22 was repeated using as starting material the product of Example 23.

EXAMPLE 25

Fourth Cycle Rehydration

Example 22 was repeated using as starting material the product of Example 24. The resulting calcined material had the XRD pattern shown in Table XRD-15, and had $^{27}Al$ nmr peaks at 67.6 and 11.0 ppm.

EXAMPLE 26

Fifth Cycle Rehydration

Example 22 was repeated using as starting material the product of Example 25.

EXAMPLE 27

Sixth Cycle Rehydration

Example 22 was repeated using as starting material the product of Example 26.

EXAMPLE 28

Example 22 was repeated but this time carbon dioxide was bubbled through undecarbonated distilled water. The XRD pattern was that of a regenerated anionic double hydroxide clay. Carbonate was confirmed to be the interlayer anion from fourier transform i.r and microanalysis of carbon.

EXAMPLES 29 TO 33

Figure 2:
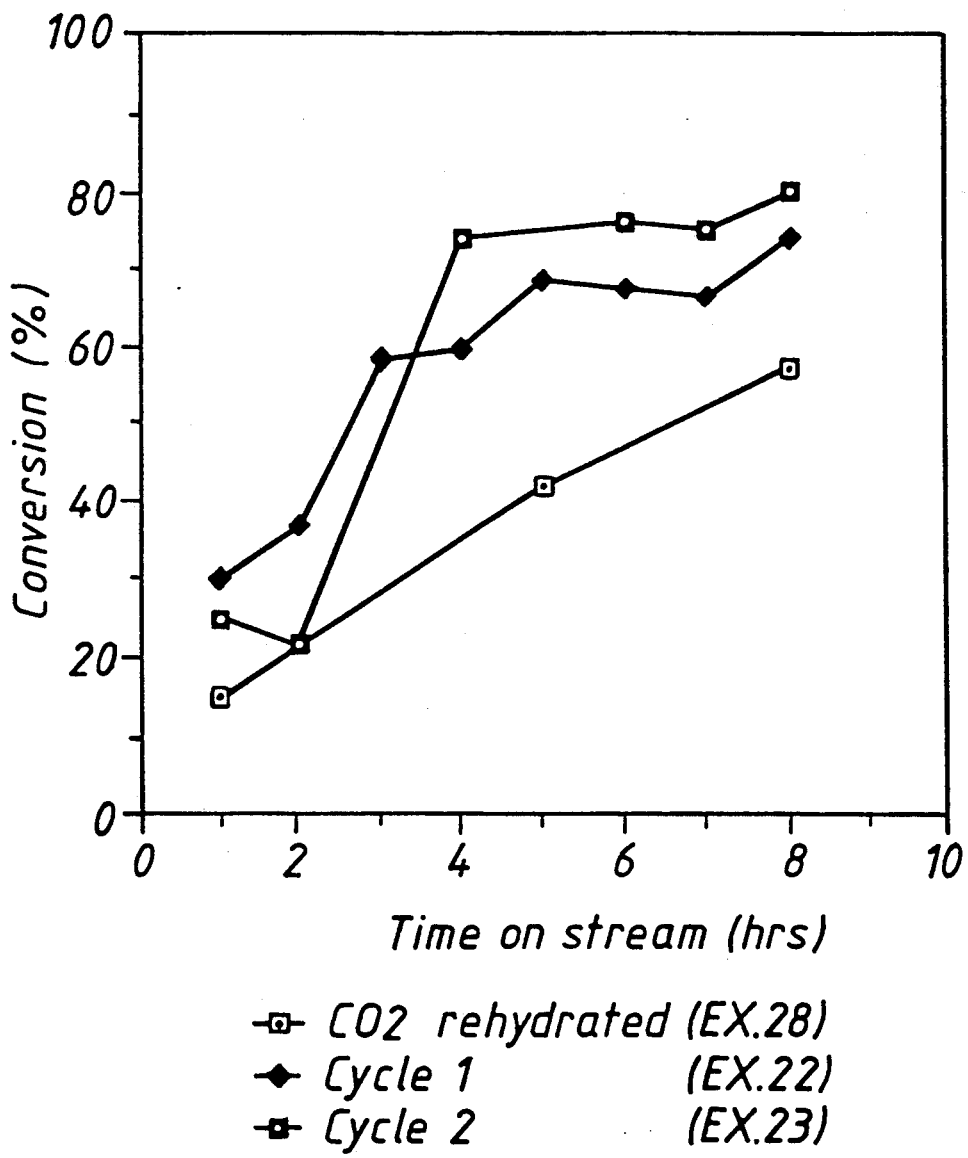
FIG. 2 is a graph showing the percent of conversion of propylene oxide versus the time on stream for glycol ether preparation using the method of the present invention and using a method which is a variation of the present invention.

The general method of glycol ether preparation described in Example 10 was carried out using as catalysts the rehydrated-recalcined products of Examples 22, 23, 25, 27 and 28 and using ethanol/propylene oxide 10/1 as feedstock. Details are given below. In each case, only traces (less than 70 ppm) of products other than 2° and 1° glycol ethers were obtained. The results are summarised graphically in FIGS. 1 and 2. FIG. 1 also includes the results of Example 10, i.e. using a catalyst which has not been rehydrated and calcined. It can be seen that rehydration-recalcination produces extremely beneficial effects.

EXAMPLE 29

The calcined material of Example 22 was tested: weight-6.7 g, volume-9 ml, temperature-120° C., feed rate-10.5 ml/hr, pressure-15 bar. The results are given in Table 1.

TABLE 1

Results of Example 29

| Time on stream (hours) | % conversion of propylene oxide | 2° Product selectivity |
|---|---|---|
| 1 | 30 | 83 |
| 2 | 37 | 95 |
| 3 | 58 | 86 |
| 4 | 59 | 89 |
| 5 | 68 | 88 |
| 6 | 67 | 93 |
| 7 | 66 | 90 |
| 8 | 74 | 88 |

EXAMPLE 30

The calcined material obtained in Example 23 was tested. Weight-4.4 g, volume-6 ml, temperature-120° C., feed rate-7.2 ml/hr, pressure-15 bar. The results are given in Table 2.

TABLE 2

Results of Example 30

| Time on stream (hours) | % conversion of propylene oxide | 2° Product selectivity |
|---|---|---|
| 1 | 25 | 100 |
| 4 | 74 | 84 |
| 6 | 76 | 84 |
| 8 | 76 | 88 |
| 10 | 75 | 81 |
| 13 | 80 | 84 |

EXAMPLE 31

The calcined material obtained in Example 25 was tested. Weight-5.4 g, volume-5 ml, temperature-120° C., feed rate-7.5 ml/hr, pressure-15 bar. The results are given in Table 3.

TABLE 3

Results of Example 31

| Time on stream (hours) | % conversion of propylene oxide | 2° Product selectivity |
|---|---|---|
| 1 | 11 | 100 |
| 4 | 61 | 85 |
| 6 | 59 | 85 |
| 8 | 65 | 83 |
| 10 | 63 | 89 |

EXAMPLE 32

The calcined material obtained in Example 27 was tested. Weight-7.3 g, volume-10 ml, temperature-120° C., feed rate-15 ml, pressure-15 bar. The results are given in Table 4.

TABLE 4

| | Results of Example 32 | |
|---|---|---|
| Time on stream (hours) | % conversion of propylene oxide | 2° Product selectivity |
| 1 | 15 | 87 |
| 2 | 14 | 87 |
| 3 | 16 | 86 |
| 4 | 23 | 88 |
| 5 | 46 | 89 |
| 6 | 45 | 88 |
| 7 | 52 | 87 |
| 9 | 53 | 86 |

EXAMPLE 33

The calcined material obtained in Example 28 was tested. Weight-6.2 g, volume-9 ml, temperature-120° C., feed rate-10.5 ml/hr, pressure-15 bar. The results are given in Table 5.

TABLE 5

| | Results of Example 33 | |
|---|---|---|
| Time on stream (hours) | % conversion of propylene oxide | 2° Product selectivity |
| 2 | 15 | 89 |
| 5 | 42 | 82 |
| 8 | 57 | 86 |

EXAMPLE 34 (COMPARATIVE)

This Example uses a conventional cationic clay catalyst in the preparation of a glycol ether. The catalyst was a fully hydrogen-ion exchanged clay, with no residual mineral acid, as described in EP-A-31687. The general method of Examples 10 to 18 was used, with the following conditions:

Starting reactant mole ratio ethanol/propylene oxide 10/1. Catalyst H+ - montmorillonite, weight - 7.4 g, volume - 10 ml, particle size - 0.5-1.0 mm, pressure - 15 barg.

The results are given in Table 6, and clearly show that, while the prior art catalyst is very active in the reaction, it is very much less selective than the catalysts used in the present invention. The comparative tests were carried out at two different flow rates (LHSV=liquid hourly space velocity) and temperatures to illustrate this point.

TABLE 6

| | Results of Comparative Example 34 | | | |
|---|---|---|---|---|
| Time on stream (hours) | LHSV (h$^{-1}$) | T/°C. | % conversion of propylene oxide | 2° Product selectivity |
| 2 | 1 | 80 | 97 | 41 |
| 23 | 1 | 120 | 98 | 35 |
| 29 | 2 | 120 | 99 | 37* |

*The residual oxygenate products other than 1-ethoxypropan-2-ol and 2-ethoxypropan-1-ol, total around 1700 ppm, measured by gas chromatography and mass spectrometry.

In the following tables of X-ray diffraction data, VS=very strong, S=strong, FS=fairly strong, M=medium, W=weak, VW=very weak and B=broad.

TABLE XRD-1

| Powder X-ray diffraction data for uncalcined sample from Example 1 | |
|---|---|
| d/Å | Relative Intensity (I/I$_o$) |
| 7.8 | VS |
| 3.9 | S |
| 2.6 | S |
| 2.3 | W |
| 1.9 | W |
| 1.53 | S |
| 1.50 | FS |

TABLE XRD-2

| Powder X-ray diffraction data for uncalcined sample from Example 2 | |
|---|---|
| d/Å | Relative Intensity (I/I$_o$) |
| 8.2 | VS |
| 4.0 | S |
| 2.7 | S |
| 2.4 | W |
| 2.0 | W |
| 1.57 | S |
| 1.54 | M |

TABLE XRD-3

| Powder X-ray diffraction data for uncalcined sample from Example 3 | |
|---|---|
| d/Å | Relative Intensity (I/I$_o$) |
| 7.9 | VS |
| 3.9 | S |
| 2.6 | S |
| 2.3 | W |
| 1.9 | W |
| 1.53 | S |
| 1.50 | FS |

TABLE XRD-4

| Powder X-ray diffraction data for uncalcined sample from Example 4 | |
|---|---|
| d/Å | Relative Intensity (I/I$_o$) |
| 7.7 | S |
| 3.8 | M |
| 2.7 | BS |
| 2.3 | W |
| 1.56 | BM |

TABLE XRD-5

| Powder X-ray diffraction data for uncalcined sample from Example 5 | |
|---|---|
| d/Å | Relative Intensity (I/I$_o$) |
| 7.8 | VS |
| 4.5 | FS |
| 3.8 | S |
| 2.6 | S |
| 2.3 | BM |
| 2.0 | BM |
| 1.48 | M |
| 1.45 | M |

TABLE XRD-6

| Powder X-ray diffraction data for calcined Mg—Al sample from Example 6 reference A | |
|---|---|
| d/Å | Relative Intensity (I/I$_o$) |
| 2.6 | BW |
| 2.1 | S |
| 1.5 | FS |
| 1.2 | W |

TABLE XRD-7

Powder X-ray diffraction data for calcined Mg—Fe sample from Example 6 reference B

| d/Å | Relative Intensity (I/I₀) |
|---|---|
| 2.13 | BS |
| 1.50 | BS |

TABLE XRD-8

Powder X-ray diffraction data for calcined Ni—Al sample from Example 6 reference C

| d/Å | Relative Intensity (I/I₀) |
|---|---|
| 2.4 | BS |
| 2.1 | S |
| 1.5 | S |
| 1.3 | W |
| 1.2 | W |

TABLE XRD-9

Powder X-ray diffraction data for calcined Zn—Cr sample from Example 6 reference D

| d/Å | Relative Intensity (I/I₀) |
|---|---|
| 3.0 | W |
| 2.8 | S |
| 2.6 | S |
| 2.5 | VS |
| 2.1 | W |
| 1.9 | W |
| 1.6 | M |
| 1.5 | M |
| 1.38 | M |
| 1.36 | W |

TABLE XRD-10

Powder X-ray diffraction data for calcined Li—Al sample from Example 6 reference E

| d/Å | Relative Intensity (I/I₀) |
|---|---|
| 2.5 | BW |
| 2.0 | BW |
| 1.5 | BW |
| 1.4 | BW |

TABLE XRD-11

Powder X-ray diffraction data for rehydrated sample from Example 16

| d/Å | Relative Intensity (I/I₀) |
|---|---|
| 7.8 | VS |
| 3.9 | S |
| 2.6 | S |
| 2.3 | W |
| 1.9 | W |
| 1.53 | S |
| 1.50 | FS |

TABLE XRD-12

Powder X-ray diffraction data for calcined sample from product in Example 16. Starred (*) values due to spinel (MgAl₂O₄) and the unstarred due to anionic double hydroxide clay.

| d/Å | Relative Intensity (I/I₀) |
|---|---|
| 2.4* | W |
| 2.1 | S |
| 2.0* | FS |
| 1.6* | W |
| 1.5 | FS |
| 1.4* | FS |

TABLE XRD-13

Powder X-ray diffraction data for rehydrated sample from Example 17. Starred (*) values due to spinel (MgAl₂O₄) and the unstarred due to anionic double hydroxide clay.

| d/Å | Relative Intensity (I/I₀) |
|---|---|
| 7.8 | VS |
| 3.9 | S |
| 2.6 | S |
| 2.4* | W |
| 2.3 | FS |
| 2.02* | W |
| 1.98 | W |
| 1.53 | FS |
| 1.50 | S |
| 1.4* | FS |

TABLE XRD-14

Powder X-ray diffraction data for calcined sample from Example 17. Starred (*) values due to spinel (MgAl₂O₄) and the unstarred due to anionic double hydroxide clay.

| d/Å | Relative Intensity (I/I₀) |
|---|---|
| 4.7* | W |
| 2.8* | W |
| 2.4* | FS |
| 2.1 | S |
| 2.0* | S |
| 1.6* | S |
| 1.5 | S |

TABLE XRD-15

Powder X-ray diffraction data for calcined product in Example 21. Starred (*) values due to spinel and the unstarred due to anionic double hydroxide clay.

| d/Å | Relative Intensity (I/I₀) |
|---|---|
| 4.7* | W |
| 2.9* | W |
| 2.4* | S |
| 2.1 | S |
| 2.0* | S |
| 1.6* | VW |
| 1.5 | W |
| 1.4* | S |

We claim:

1. A process for the preparation of a glycol ether by reacting an olefin oxide with an excess of an alcohol over a catalyst; characterized in that the catalyst comprises a material which has been prepared by calcination of an anionic double hydroxide clay having a structure comprising magnesium and aluminum in combination, following by rehydration and subsequent recalcination.

2. A process as claimed in claim 1, in which the olefin oxide has up to 10 carbon atoms.

3. A process as claimed in claim 1, in which the alcohol has up to 8 carbon atoms.

4. A process as claimed in claim 1, in which ethanol is reacted with propylene oxide.

5. A process as claimed in claim 1, carried out at a temperature of from 0° to 200° C.

6. A process as claimed in claim 1, in which the calcination of the anionic double hydroxide clay comprised heating to a temperature of from 300° to 550° C. under non-reducing conditions.

7. A process as claimed in claim 6, in which the calcination of the anionic double hydroxide clay comprised heating in air.

8. A process as claimed in claim 8, in which the rehydration has been carried out using water substantially free from dissolved ions.

9. A process as claimed in claim 2 in which the alcohol has up to 8 carbon atoms.

* * * * *